United States Patent [19]

Warriner

[11] Patent Number: Plant 6,972

[45] Date of Patent: Aug. 8, 1989

[54] ROSE PLANT JACLOY

[75] Inventor: William A. Warriner, Tustin, Calif.

[73] Assignee: Jackson & Perkins Company, Medford, Oreg.

[21] Appl. No.: 228,595

[22] Filed: Aug. 4, 1988

[51] Int. Cl.[4] ..... A01H 5/00

[52] U.S. Cl. ..... Plt./24

[58] Field of Search ..... Plt./24

*Primary Examiner*—James R. Feyrer

*Attorney, Agent, or Firm*—Majestic, Parsons, Siebert & Hsue

[57] ABSTRACT

A rose variety of the floribunda class is provided that bears bright non-fading yellow color flowers with medium length stems, and a dull medium green foliage that is susceptible to powdery mildew, and sharp reddish thorns.

1 Drawing Sheet

SUMMARY OF THE INVENTION

The present invention relates to a new and distinct variety of rose plant of the floribunda class, which was originated by me by crossing the variety Kortime, U.S. Plant Pat. No. 4,044, with an unnamed seedling.

The primary objective of this breeding was to produce a new rose variety of the floribunda class having similar flower color to the variety Kortime, but with the more pointed bud found in the unnamed seedling parent. This objective was substantially achieved, along with other desirable improvements, as evidenced by the following unique combination of characteristics which are outstanding in the new variety and which distinguish it from its parents as well as from all other varieties of which I am aware. For example, this new variety has:

1. A bright yellow, non-fading flower;
2. A pointed bud;
3. An abundance of sharp thorns;
4. Dull medium green foliage; and
5. A high production of medium length stems.

Asexual reproduction of this new variety by budding, as performed at Wasco, Calif., shows that the foregoing characteristics and distinctions come true to form and are established and transmitted through succeeding propagations.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which has been denominated "Jacloy". Color terminology is in accordance with The Royal Horticultural Society Colour Chart except where an ordinary dictionary significance for the color is apparent.

Observations of the buds and flowers were made from specimens grown in a garden at Irvine, Calif.

Flower

This rose plant variety produces yellow colored flowers that, unlike most other yellow cut flowers, do not fade.

The blooming habit is recurrent. The bud size is one and one-half inches when the petals start to unfurl. Unlike the Kortime variety, which has a blunt or flat bud tip, the bud form is pointed ovoid. The bud color when sepals first divide is near Yellow Group 13B. When half blown, the upper side of petals is near Yellow Group 13B to Yellow Group 13C. The lower side of petals is near Yellow Group 13B to Yellow Group 13C. The sepals have a color near Green Group 138A. The surface texture is covered with fine hairs. There are three normally appendaged sepals, and two unappendaged sepals with a hairy edge. The receptacle color is near Green Group 138A and it has a funnel shape, small size and smooth surface. The peduncle is of short length and has a glandular surface. Peduncle color is medium green and the peduncle is stiff and erect.

Bloom

Bloom size is medium, with an average open size of three and one-half inches, born singly. The stems are strong and medium in length. The form when first open is high center and is retained to the end. The outer petals curl back quill fashion. Under normal conditions there are 35 to 40 petals. The upper side and the reverse side of the petals at the flower center are both near Yellow Group 13B to Yellow Group 13C. The major color on the upper and lower sides is near Yellow Group 13B. There are no variegations. The general tonality at the end of the first day shows no change in color. At the end of the third day, there is still no change in color. This retention of color is unusual for yellow roses, especially when cut.

The fragrance is slight. The petal texture is thick. The petal shape is round and slightly notched. The petal form has slightly recurved tips and slightly quilled edges.

The arrangement is imbricated with no pentaloids in the center. The blooms drop off cleanly, and last both on the plant and as a cut flower for a long time.

Reproductive Parts

There are many anthers of medium size, of yellow color and arranged regularly around the styles. The filaments are yellow, the pollen is gold yellow, the styles are greenish white, and the stigmas are greenish white.

Plant

The plant has vigorous, upright growth of bush form.

Foliage

The foliage is medium size and normal in quantity. The new foliage is reddish colored. The old foliage is medium green and is dull. Normal mid-stem leaves have five leaflets.

The leaflets have an oval pointed shape, are smooth textured, and have a double serrated edge. Petiole rachis is green, and petiole underside is rough, with prickles. Stipules are medium and bearded. The foliage is susceptible to mildew under normal growing conditions at Irvine, Calif.

Wood

New wood is reddish colored with a smooth bark. Old wood is green with a smooth bark.

Prickles

There are many prickles on the main canes from the base and on the laterals from the main canes. The prickles are medium, straight and very sharp. The prickles are red colored when young. There are no small prickles on the main stalks or laterals.

Parentage

The seed parent was of the variety Kortime. The pollen parent was an unnamed seedling.

Classification

Botanical is rosa hybrid. Commercial is floribunda.

I claim:

1. A new and distinct variety of rose plant of the floribunda class substantially as herein shown and described, characterized particularly as to novelty by high production of medium length stems, bright non-fading yellow color, pointed ovoid bud, dull medium green powdery mildew susceptible foliage, and an abundance of very sharp reddish thorns.

* * * * *

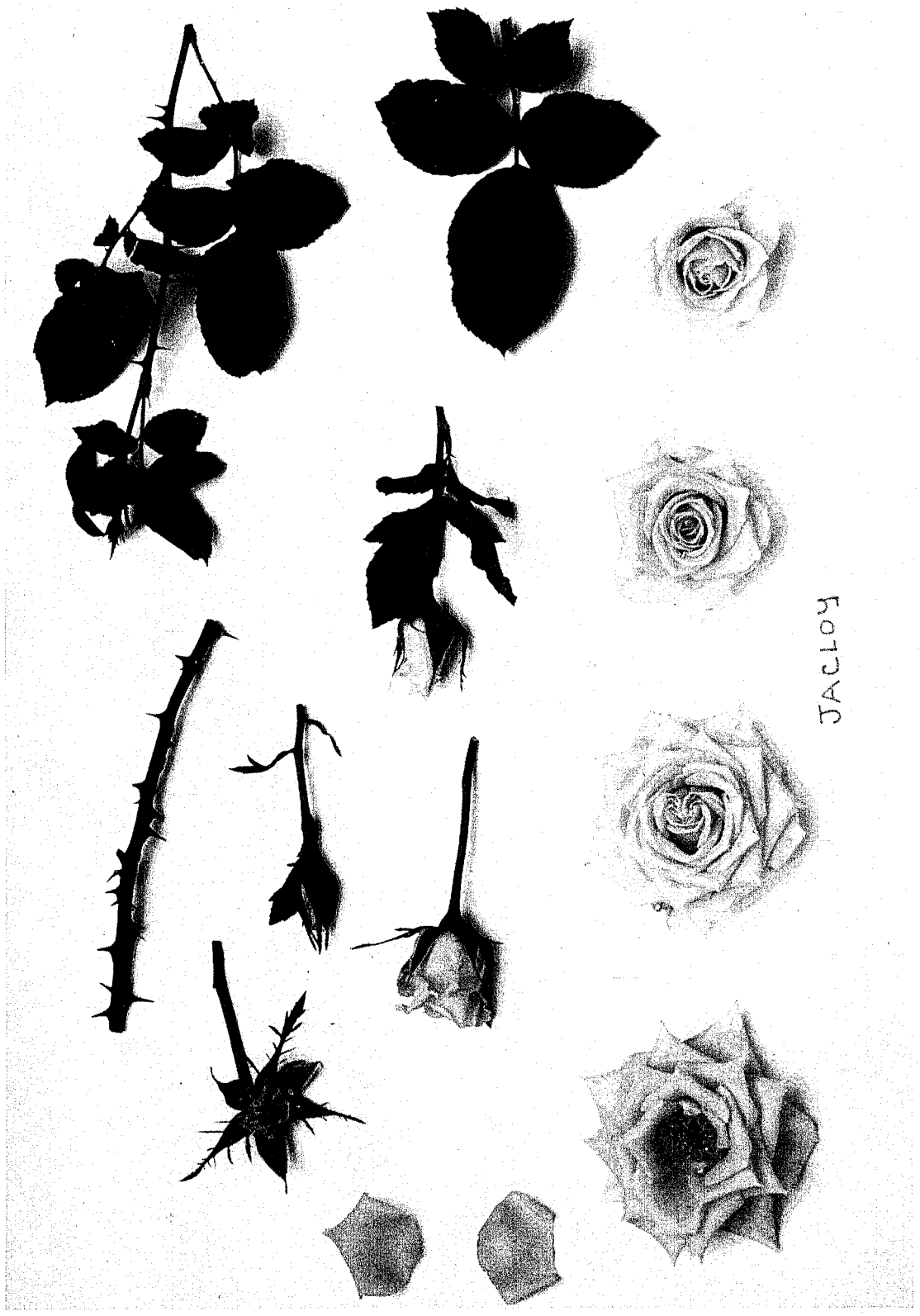
JACLOY